United States Patent [19]
Andermann et al.

[11] Patent Number: 4,459,292
[45] Date of Patent: Jul. 10, 1984

[54] THERAPEUTIC COMPOSITIONS FOR THE TREATMENT OF ACCOMMODATION PROBLEMS OF THE EYE AND METHOD OF USING INOSINE MONOPHOSPHATE

[75] Inventors: Guy Andermann; Claudine Andermann, both of Colmar, France

[73] Assignee: Laboratoires POS, Kaysersberg, France

[21] Appl. No.: 454,472

[22] Filed: Dec. 28, 1982

[30] Foreign Application Priority Data

Dec. 30, 1981 [FR] France ................................ 81 24476

[51] Int. Cl.³ ............................................. A61K 31/70
[52] U.S. Cl. ...................................... 424/180; 536/28
[58] Field of Search ................... 424/180; 536/28, 27, 536/29

[56] References Cited

U.S. PATENT DOCUMENTS

| | | | |
|---|---|---|---|
| 3,152,116 | 10/1964 | Broida | 536/27 |
| 4,136,175 | 1/1979 | Rideout et al. | 424/180 |
| 4,208,406 | 6/1980 | Lapinet et al. | 424/180 |
| 4,287,175 | 9/1981 | Katz | 424/180 |

Primary Examiner—Johnnie R. Brown
Attorney, Agent, or Firm—Browdy and Neimark

[57] ABSTRACT

A new composition consists of an eyewash in buffered saline solution, preferably aqueous having the desired isotonicity and in which the active agent consists of inosine monophosphate, preferably in the form of a disodium salt. It is applied to the treatment of human eye troubles such as: strabismus of various types, beginning presbyopia, heterophoria by convergence insufficiency exophoria, asthenopia by ametropia, fusion troubles in astigmats.

17 Claims, No Drawings

THERAPEUTIC COMPOSITIONS FOR THE TREATMENT OF ACCOMMODATION PROBLEMS OF THE EYE AND METHOD OF USING INOSINE MONOPHOSPHATE

FIELD OF INVENTION

This invention relates to eye treatment and especially concerns a therapeutic pharmaceutical composition for treating accommodation difficulties of the human eye such as strabismus, presbyopia, heterophoria, etc.

BACKGROUND

Inosine monophosphate is a nucleotide well known in itself, used for example as a potentiator of certain food flavorings, especially in association with guanosine monophosphate. Moreover, several investigators have indicated that inosine, itself, used intramuscularly or intravenously, is endowed with cardiac analeptic activity and could be used in the treatment of cardiac insufficiency in man. However, insofar as is known, no specific therapeutic application of inosine monophosphate per se has been described to date.

However, for treatments of the eye, medicinal associations of various biochemical elements have already been recommended including, in particular, a very specific combination, for the local treatment of cataracts, containing the ingredients: nicotinamide, sodium succinate, magnesium L-aspartate and, possibly, sodium glycerophosphate, and including inosine monophosphate.

SUMMARY

Surprisingly, it has now been found that only one of these compounds, namely inosine monophosphate, has a beneficial effect in the treatment of numerous vision troubles and that an eyewash with a base of this active product appreciably corrects the AC/A ratio (wherein A=Accommodation and C=Convergence) of a troubled eye for several months after treatment.

According to the invention, an eyewash type composition for the treatment of accommodation troubles of the eye includes a buffered saline solution, exhibiting the desired isotonicity and containing as active agent an effective amount of inosine monophosphate or of a pharmaceutically acceptable sodium salt of this compound.

DETAILED DESCRIPTION OF EMBODIMENTS

This eyewash does not exhibit the known drawbacks of short effective period, local intolerance, systemic toxicity, inherent in the use of eyewashes with a base of myotic substances such as, for example, phospholine iodide, difluorophate or even eserin.

Although the normal physiological pH range of the human eye is 7.3 to 7.4, the solutions for treatment of the eyes or eyewashes can exhibit, depending on the stability of the various constituents, a pH from 3 to 9, preferably from 5.5 to 8.0. For the eyewash of the invention to remain very stable, it is preferable to keep the pH between 6.2 and 7.5.

Any pharmaceutically acceptable buffer system can be added to the eyewash to maintain the desired pH. Of usable buffers there can be mentioned: sodium borate, boric acid, disodium monohydrogen phosphate, sodium dihydrogen phosphate, a citrate buffer composed of sodium citrate and citric acid or an acetate buffer composed of acetic acid and sodium acetate, and associations of phosphate and citrate buffers.

The salinity of the prepared solution is preferably isotonic, which is equivalent to 0.9% sodium chloride, but it can vary from 0.8 to 1.0%, a concentration which is moderately isotonic in the composition. Any pharmacologically acceptable salt can be used to maintain the desired isotonicity of the solution obtained. As the isotonic requirements can vary from one patient to another, the desired isotonicity for any patient can be obtained by increasing or reducing the amount of salt contained in the solution. Pharmocologically acceptable nonionic water soluble bodies, instead of a salt, can be added to maintain or obtain the desired isotonicity. By way of non-limiting illustration, polyethyleneglycol and polypropyleneglycol can be mentioned among these nonionic bodies.

Additionally, it unexpectedly has been found that when inosine monophosphate is used alone and not in association with other compounds such as, for example, nicotinamide, sodium succinate, sodium glycerophosphate, magnesium L-aspartate or sodium chloride, the preparation is much more stable, both from the bacteriological viewpoint and the physico-chemical viewpoint. This improvement prevents bacterial contamination and transformation of the inosine monophosphate into hypoxanthine. Moreover, allergies of contact with certain substances are prevented.

The aqueous solutions suitable for topical administration in the eye can contain about 0.01 and 0.2% by weight of a sodium salt of the appropriate inosine monophosphate. It is recommended to apply them to the eye at a rate of 1 to 4 times per day for a treatment period of at least a month.

The invention will be better understood by the description below relating, on the one hand, to a series of nonlimiting examples of eyewashes able to meet the desired objectives and, or the other hand, to suit the results of clinical work performed with such compositions having an inosine monophosphate base.

(A) Examples of Compositions According to the Invention

Aqueous solutions of eyewash suitable for topical administering are shown below:

EXAMPLE 1

Inosine monophosphate, disodium salt: 0.1 g
Sodium chloride: 0.85 g
Disodium edetate: 0.02 g
Phosphate buffer (at pH 6.0): 0.1 g
Benzalkonium chloride: 0.005 g
Water, Sufficient for: 100 ml

EXAMPLE 2

Inosine monophosphate, disodium salt: 0.1 g
Sodium chloride: 0.85 g
Disodium edetate: 0.02 g
Hydroxyethylcellulose: 0.3 g
Polyvinyl alcohol: 0.1 g
Phosphate buffer (at pH 6.0): 0.1 g
Benzalkonium chloride: 0.005 g
Water, Sufficient for: 100 ml

EXAMPLE 3

Inosine monophosphate, disodium salt: 0.1 g
Sodium chloride: 0.85 g
Disodium edetate: 0.02 g Phosphate buffer (at pH 6.0): 0.1 g
Thimerosal: 0.010 g
Water, Sufficient for: 100 ml

EXAMPLE 4

Similar to example II, except that the benzalkonium chloride (0.005 g) is replaced with thimerosal (0.010 g).

EXAMPLES 5 TO 8

Similar to examples 1 to 4, respectively, except that the phosphate buffer is replaced in each case with a borate buffer (at pH 6.0).

EXAMPLE 9

Inosine monophosphate, disodium salt: 0.05 g
Sodium chloride: 0.85 g
Disodium edetate: 0.02 g
Acetate buffer (at pH 6.0): 0.1 g
Benzalkonium chloride: 0.005 g
Water, Sufficient for: 100 ml

EXAMPLE 10

Inosine monophosphate, disodium salt: 0.1 g
Chlorhexidine digluconate: 0.005 g
Sodium chloride: 0.9 g
Purified water, Sufficient for: 100 ml Thus, as can be seen, compositions according to the invention can contain known sterilizing, antiseptic and/or preservative agents such as, for example, benzalkonium chloride, thimerosal, chlorhexidine gluconate, etc.

(B) Clinical experiments

Numerous experiments on patients exhibiting accommodation troubles of the eye were undertaken and are summarized as follows (on the basis of aqueous eyewashes corresponding to the examples above).

(b1) Difficulties in Oculomotor Balance

The effect of an eyewash of the type in example No. 10 above was studied on 45 cases distributed as follows: 7 normal cases, 7 asthenopic cases, 8 heterophoric subjects, 8 presbyopic subjects and 14 strabismic subjects.

To verify objectively the effect of the eyewash with inosine monophosphate, a measurement of the AC/A ratio was made. In every case, the administrations of the eyewash with IMP were twice a day for 10 to 15 days.

The results of this work (in percentage of treated cases):

82.0% of the patients obtained a favorable change in the AC/A ratio 97.5% of the subjects reported feeing a subjective improvement 2.5% of the patients did not exhibit a therapeutic or subjective improvement.

This study shows the beneficial effect of the eyewash on the ratio which links accommodation and convergence. Given the accommodation-convergence synkinesis, the ease of accommodation reduces the associated convergence; the high ratio is thus normalized in asthenopia, heterophoria of the convergence insufficiency type and in accommodative esotropia. In other cases (presbyopia, exophoria), the lowered ratio is again normalized, it seems, by the ease of accommodation.

Overall, it can be concluded that the pharmacodynamic effect is comparable to that of the myotics, but without exhibiting their drawbacks,

(b2) Binocular Vision Troubles

The effect of the eyewash according to example No. 10 was tested on 40 patients affected with strabismus (10 cases), presbyopia (8 cases), heterophoria (8), asthenopia (70, various eye defects (7).

The value of the AC/A ratio was determined with an acameter. Every patient received 2 administrations per day for 2 weeks, then every other day, such treatment having been prolonged in the cases of strabismus.

The results of this work showed that:

33 patients, or 82.5%, obtained a favorable change in the AC/A ratio 7 patients, or 17.5%, did not exhibit any changes in the AC/A ratio, but the AC/A ratio was kept, in every case, within normal or near-normal values. Moreover, these patients all exhibited an improvement relating to their accommodation and convergence curve or their asthenopia.

(b3) Fusion Troubles with Astigmats

An eyewash with inosine monophosphate according to the invention was tested using the double-blind technique on 95 patients. Each patient underwent test series including: a measurement of the visual acuity, skiascopy, ophthalmometry, measurement of the fusion (Berens rule), measurement of the AC/A ratio (using an acameter).

The patients exhibited a lowered fusion range, an astigmatism of 0.25 at 4 dioptres and a greatly disturbed AC/A ratio. They were divided into two groups, the first (I) being treated with eyewash according to the invention while the second (II) was treated with the double-blind technique first with a placebo eyewash, then with the eyewash with inosine monophosphate.

The following results were obtained:

For group I: 88.2% obtained very good functional results; 97.5% obtained improvement on the fusion and 85.8% obtained normal ratio for the AC/A For group II: unchanged results for the three said types of criteria but, after treatment with the eyewash of the invention, a significant improvement of these criteria in all the subjects.

The sustained benefit of such an eyewash in the treatment of fusion troubles of the astigmat and the normalization of binocular vision can be concluded, thus preventing the wearing of corrective lenses.

(b4) Use in Orthoptics

Here the study dealt with 72 subjects from 2 to 20 years of age who exhibited strabismus either by convergence insufficiency or esotropia or by post-operative residual esotropia; the values of the objective angles (measured with a synoptophore) and the subjective angles were studied and systematically noted—by ophthalmological and orth optical examinations before, during and after treatment—so as to be able to establish the normal and abnormal retinal correspondences.

The children or adolescents were separated into two groups of which: group I contained 55 subjects who received administrations of eyewash according to the invention at a rate of 1 drop two to three times per day in both eyes (variable periods-2 weeks to 12 months or longer); group II was composed, on the one hand, of 17 subjects never having received any administration of eyewash and, on the other hand, 32 subjects from group I considered as controls for the period preceding the prescribing of eyewash according to the invention.

Thus, 104 observations on 72 patients were able to be made of which it will be noted that the majority were already treated for months by optical correction and that some had suffered failures with the standard methods with other eyewashes.

It was first noted during the treatments that the administrations of eyewash with inosine monophosphate were well tolerated and caused neither irritation nor affected the cornea. Moreover, it is interesting to note that myosis was not found, as is the case during the known treatment by myotic eyewashes which cause considerable visual trouble.

To note the results obtained, a classification of the type was established:

very good result when the angle disappeared or significantly decreased;

medium result when the angle decreased slightly;

no result when the angle kept approximately its beginning value.

Thus, it could be established that with the patients treated with the eyewash according to the invention, very good results were obtained in nearly 50% of the observations and medium results were achieved in more than 30% of the observations. It can be concluded that the eyewash with the inosine monophosphate has an undeniable effect on the angles of the squinters and on the residual angles of strabismic patients operated on for this deformation.

The foregoing description of the specific embodiments will solely reveal the general nature of the invention that others can by applying current knowledge, ratherly modify and/or adapt for various applications such specific embodiments without departing from the generic concept, and, therefore, such adaptations and modifications should and are intended to be comprehended within the meaning and range of equivalents of the disclosed embodiments. It is to be understood that the phrasiology of terminology employed herein is for the purpose of description and not of limitation.

What is claimed is:

1. A therapeutic composition for the treatment of accommodation of the human eye in the form of an eyewash in an isotonic buffered saline solution, including as active agent an effective amount for the treatment of accommodation of the human eye of inosine monophosphate or a pharmaceutically acceptable sodium salt thereof, with the proviso that said composition does not contain nicotinamide, sodium succinate and magnesium L-aspartate.

2. The composition according to claim 1, comprising 0.01 to 0.2% disodium salt of inosine monophosphate, in relation to the total weight of the eyewash.

3. The composition according to claim 1 in the form of a buffered aqueous solution with pH between 5.5 and 8 wherein the isotonic solution comprises a sodium chloride content of 0.8 to 1% based on the weight of the composition.

4. The composition according to claim 1, further containing a sterilizing, antiseptic or preservative agent of the group consisting of: benzalkonium chloride, thimerosal, chlorohexidine gluconate, or mixtures thereof.

5. The composition according to claim 2 in the form of a buffered aqueous solution with pH between 5.5 and 8, wherein the isotonic solution comprises a sodium chloride content of 0.8 to 1% based on the weight of the composition.

6. The composition according to claim 1 in the form of a buffered aqueous solution with pH between 6.2 and 7.5, wherein the isotonic solution comprises a sodium chloride content of 0.8 to 1% based on the weight of the composition.

7. The composition according to claim 2 in the form of a buffered aqueous solution with pH between 6.2 and 7.5, wherein the isotonic solution comprises a sodium chloride content of 0.8 to 1% based on the weight of the composition.

8. The composition according to claim 2, further containing a sterilizing, antiseptic or preservative agent of the group consisting of: benzalkonium chloride, thimerosal, chlorohexidine gluconate, or mixtures thereof.

9. The composition according to claim 3, further containing a sterilizing, antiseptic or preservative agent of the group consisting of: benzalkonium chloride, thimerosal, chlorohexidine gluconate, or mixtures thereof.

10. The composition according to claim 5, further containing a sterilizing, antiseptic or preservative agent of the group consisting of: benzalkonium chloride, thimerosal, chlorohexidine gluconate, or mixtures thereof.

11. The composition according to claim 6, further containing a sterilizing, antiseptic or preservative agent of the group consisting of: benzalkonium chloride, thimerosal, chlorohexidine gluconate, or mixtures thereof.

12. The composition according to claim 7, further containing a sterilizing, antiseptic or preservative agent of the group consisting of: benzalkonium chloride, thimerosal, chlorohexidine gluconate, or mixtures thereof.

13. An eyewash composition for the treatment of accommodation of the human eye consisting essentially of inosine monophosphate or a pharmaceutically acceptable sodium salt thereof as active agent, said active agent being present in an amount effective for the treatment of accommodation of the human eye, and a buffered aqueous saline solution as a pharmaceutical carrier for said active agent.

14. An eyewash composition according to claim 13 having a pH between 6.2 and 7.5, a sodium chloride content of 0.8 to 1%, and further containing a preservative-effective amount of an antiseptic agent which is non-irritating to the eye in the quantity present in said eyewash.

15. A method for the treatment of accommodation of the human eye comprising dropping in the eye of a patient in need of said therapy an eyewash composition containing an amount effective for the treatment of accommodation of the human eye of inosine monophosphate or a pharmaceutically acceptable sodium salt thereof.

16. A method according to claim 15 wherein said patient is suffering from strabismic, beginning presbyopia, heterophoria by convergence insufficiency, exophoria, asthenopia by ametropia, or fusion difficulties where said patient is an astigmat.

17. A method of treating the eye of a patient in need of treatment with the therapeutic composition of claim 1 comprising administering said eyewash to said eye with an effective amount of said eyewash.

* * * * *